US008641193B2

(12) United States Patent
Jiao et al.

(10) Patent No.: US 8,641,193 B2
(45) Date of Patent: Feb. 4, 2014

(54) SPECTRAL CONTRAST FOR GLAUCOMA IMAGING

(75) Inventors: Shuliang Jiao, Miami, FL (US); Xiangrun Huang, Wellington, FL (US); Robert W. Knighton, Duluth, MN (US)

(73) Assignee: University of Miami, Miami, FL (US)

( * ) Notice: Subject to any disclaimer, the term of this patent is extended or adjusted under 35 U.S.C. 154(b) by 312 days.

(21) Appl. No.: 13/133,016

(22) PCT Filed: Dec. 3, 2009

(86) PCT No.: PCT/US2009/066501
§ 371 (c)(1),
(2), (4) Date: Jun. 6, 2011

(87) PCT Pub. No.: WO2010/065694
PCT Pub. Date: Jun. 10, 2010

(65) Prior Publication Data
US 2011/0228223 A1 Sep. 22, 2011

Related U.S. Application Data

(60) Provisional application No. 61/119,828, filed on Dec. 4, 2008.

(51) Int. Cl.
*A61B 3/14* (2006.01)
*A61K 31/74* (2006.01)

(52) U.S. Cl.
USPC .......................... 351/206; 351/246; 424/78.04

(58) Field of Classification Search
USPC ......... 351/200, 205, 206, 221, 222, 243, 246;
382/30, 32, 33, 54; 424/78.04
See application file for complete search history.

(56) References Cited

U.S. PATENT DOCUMENTS

| 7,649,629 B2 * | 1/2010 | Rogers et al. | 356/479 |
| 2004/0075812 A1 * | 4/2004 | Kardon et al. | 351/206 |
| 2008/0266520 A1 | 10/2008 | Spaide | |
| 2009/0115964 A1 * | 5/2009 | Ueno | 351/206 |

FOREIGN PATENT DOCUMENTS

WO 2007009761 A2 1/2007

OTHER PUBLICATIONS

International Search Report and Written Opinion dated Jul. 14, 2010 for the International Application No. PCT/US2009/66501, International Filing Date Dec. 3, 2009 (consisting of 8 pages).

* cited by examiner

*Primary Examiner* — Thomas K Pham
*Assistant Examiner* — Brandi Thomas
(74) *Attorney, Agent, or Firm* — Christopher & Weisberg, P.A.

(57) ABSTRACT

A system for analyzing and detecting early stage damage to the retina related to glaucoma. The reflectance of different wavelengths of light by the retinal nerve fiber layer are compared. Changes in relative reflectance values indicate damage to the retinal nerve fibers and indicate early glaucomatous optical neuropathy.

13 Claims, 2 Drawing Sheets

SPECTRAL CONTRAST FOR GLAUCOMA IMAGING

FIELD OF THE INVENTION

The present invention relates to a method and system for contrasting the spectral reflectance of the retinal nerve fiber layer (RNFL) using optical coherence tomography (OCT).

BACKGROUND OF THE INVENTION

The optic nerve is a bundle of over a million nerve fibers that connect the retina to the brain. These nerve fibers are formed by the axons of retinal ganglion cells that extend from the retina where they detect light, to the brain where they transmit visual information. Glaucoma is a class of ocular diseases resulting from damage to the optic nerve. According to the National Eye Institute, among the United States population 40 years and older there are over 2.2 million glaucoma patients (290,000 between ages 40-49). Owing to the rapid aging of the United States population, this number may increase to more than 3 million by 2020.

Glaucoma occurs when the retinal ganglion cells disposed in the optic nerve degenerate in a characteristic and identifiable pattern, called glaucomatous optic neuropathy (GON). Untreated glaucoma may lead to permanent damage of the optic nerve resulting in vision loss, which can progress to blindness. Once vision has been lost due to glaucoma, it can never be restored.

It is known that damage to the optic nerve fibers of the Retinal Nerve Fiber Layer (RNFL) often begins years before the detectable loss of visual sensitivity as measured with visual fields. However, early, microscopic damage to the optic nerve fibers is difficult to detect in vivo. Damage to the RNFL is usually only readily detectable after vision loss has already occurred. Early detection of this damage prior to vision loss would permit early medical intervention to prevent blindness.

Increased intraocular pressure (IOP) is known to be a leading cause of GON. However, there is no set threshold of intraocular pressure that causes glaucoma. Detection of glaucoma through direct measurement of intraocular pressure is therefore not reliable. One person may develop significant nerve damage at a comparatively low intraocular pressure, while another person may have a comparatively high intraocular pressure for years and never develop nerve damage.

Current screening for glaucoma is usually performed as part of a standard eye examination. The standard eye examination for detecting glaucoma includes measuring the intraocular pressure using tonometry. However, as explained above, measuring the IOP alone is an inaccurate indicator of early onset glaucoma. Other eye exams that measure changes in size or shape of the eye, anterior chamber angle, or include visible examination of the optic nerve using a slit-lamp microscope, also lack the precision to determine microcellular damage to the RNFL. A formal visual field test is also usually performed as part of a standard eye exam to ascertain if any loss of visual sensitivity has occurred. But none of these techniques can accurately detect early microscopic signs of RNFL damage.

Optical coherence tomography (OCT) has been utilized to detect microscopic damage to the RNFL. OCT can perform micron-resolution, cross-sectional imaging of biological tissue, such as the retina. In particular, OCT uses optical interferometry to amplify light reflected from a particular depth within a partially reflective sample, in this case a retina, with a resolution governed by the coherence length of the source. Light reflected from different distances may be minimized by a number of noise reduction techniques.

Current OCT methods use a single band of light, typically centered around a wavelength of 830 nm, to discriminate the RNFL from underlying tissue based on reflectance intensity alone. Because of its cellular composition, the reflectance of RNFL is usually greater at this wavelength than the surrounding retinal tissue. This marked difference in reflectance intensity facilitates segmentation of the different layers of the retina by means of an OCT scan. In advanced glaucomatous disease, the RNFL decreases in thickness due to optic neuropathy and becomes difficult to visually discern from the surrounding tissue. This makes segmentation difficult and imprecise. In addition, normal thickness varies greatly within the RNFL, so typically a large decrease in thickness must occur before it is noticeably statistically different from normal.

The retina is comprised of several cellular layers that each have distinct reflective properties. For example, disposed between the retinal pigment epithelium and the inner limiting membrane (ILM) is the RNFL, the inner plexiform layer (IPL), and the inner nuclear layer (INL). Because of the complexity and number of retinal structures, segmenting the retinal layers may be necessary to accurately measure the reflectance from the RNFL. Such segmentation of the RNFL may be difficult due to the varying of thickness within the RNFL.

The RNFL is comprised of cylindrical fibers, making the reflectance from OCT directionally dependent. This can cause variable intensity contrast between tissue layers and thus additional difficulties in segmentation. This also causes reduced signal strength in nasal retina. Because segmentation is based solely on intensity, differences in the RNFL become difficult to discern when the RNFL becomes thin Segmentation algorithms will frequently follow retinal tissue boundaries to produce a layer identified as RNFL. However, these algorithms break down and become inaccurate when applied to retinas having damaged RNFLs. Often other retinal tissues are included in the RNFL layer as determined by the segmentation algorithms. This leads to inaccuracies and makes identifying damaged tissue unreliable.

It is therefore desirable to provide a method of accurately segmenting retinal tissues and determining the boundaries between the RNFL and surrounding tissue.

It is also desirable to provide a method for detecting early changes in the RNFL before visual sensitivity is lost, allowing early treatment to save axons.

It is also desirable to provide an OCT method that relies on spectral characteristics of the RNFL that are less sensitive to the direction of illumination and will provide a more accurate measure of the RNFL in clinical practice.

SUMMARY OF THE INVENTION

The present invention provides a method of analyzing a retina comprising applying both visible and NIR light to a retina, measuring the intensity of the light reflected from a plurality of pixels of the retina within a first band of visible light, measuring the intensity of light reflected from the plurality of pixels of the retina within a second band of NIR light and comparing the intensity of light reflected within the first band and the intensity of light reflected within the second band.

The invention also provides a method of analyzing a retina comprising performing an optical coherence tomography scan of the retina with a first beam of visible light, including measuring the intensity of the first beam reflected at a plurality of depths for each of a plurality of pixels within the retina, performing an optical coherence tomography scan of the retina with a second beam of NIR light, including measuring the intensity of the light of the second beam reflected at a plurality of depths for each of the plurality of pixels within the retina for the second beam, comparing the intensities of the reflected light of the first beam and the reflected light of the second beam.

The invention also provides an optical coherence tomographic device comprising at least one light source for producing at least a first scanning beam and a second scanning beam, an interferometer that divides the first and second scanning bands into first and second reference beams emitted toward a reference arm and first and second sample beams emitted toward a retina and then receives and combines first and second reflected reference beams and first and second reflected sample beams to produce first and second interference beams having optical intensities. The device includes an X-Y scanner for directing the first and second sample beams to a plurality of pixels on the retina, an adjustable reference mirror within the reference arm for allowing measurement of reflected light from a plurality of depths for each of the plurality of pixels and a detector for measuring the intensities of the first and the second interference beams and converting them into first and second intensity signals. The device also includes a signal processor for accumulating the first and second intensity signals for each of the plurality of pixels at each of the depths to create a three dimensional dataset.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention advantageously provides a method and system for early stage detection of glaucoma comprising a dual-band optical coherence tomography (OCT) system that utilizes both short and long wavelengths of light to detect early damage to the RNFL. The method also includes an OCT wavelength contrast method to discriminate between the RNFL and surrounding tissue, which improves the detection of RNFL tissue loss in advanced glaucoma disease.

The present invention also provides for a method of measuring retinal tissue loss resulting from glaucoma by calculating the spectral reflectance from a dual-band OCT. The measured spectral reflectance data may then be correlated to reveal tissue loss resulting from glaucomatous optic neuropathy.

The reflective properties of the RNFL differ from those of surrounding tissue. Specifically, a healthy RNFL exhibits relatively high reflectance of visible light. This increased reflectance by the RNFL of visible light, ranging between 400 and 560 nm, is more easily discerned when it is normalized against the reflectance of near infra red (NIR) light, e.g. 780-880 nm light, by the same tissue. Healthy RNFL reflects light in the 400-560 nm range at about twice the intensity it reflects light in the 780-880 nm range.

Other layers of the retina typically reflect light in the visible range at about the same intensity level that light is reflected in the near infra red (NIR) range. Thus, a healthy RNFL may be segmented from the other layers of the retina by identifying it as the region of the retina that reflects visible light at a relatively higher intensity level than NIR light.

Damage to the RNFL results in decreased reflectance of visible light particularly within the range of 480-520 nm. The intensity of reflected light in this range can be normalized by the intensity of reflected NIR light in the range of 780-880 nm Damaged RNFL can be identified as RNFL having a ratio of reflectance of visible light to reflectance of NIR light at or near 1:1.

This drop in reflectance of visible wavelengths occurs during early stages of RNFL damage, often before any noticeable loss of vision. Thus, measuring the reflectance of visible light, especially as normalized against reflectance of NIR light, may be used to identify regions of the RNFL that have been damaged even prior to actual loss of vision.

Any method of measuring the reflectance of light from the RNFL at these two bands, 480-520 nm and 780-880 nm, may be used for the present invention. OCT is readily adaptable to this invention and is thus describe in the exemplary embodiment. The invention thus provides a dual-band OCT system and method that detects early changes in retinal tissue reflectance indicative of early stages of nerve damage and glaucoma.

Figure 1:
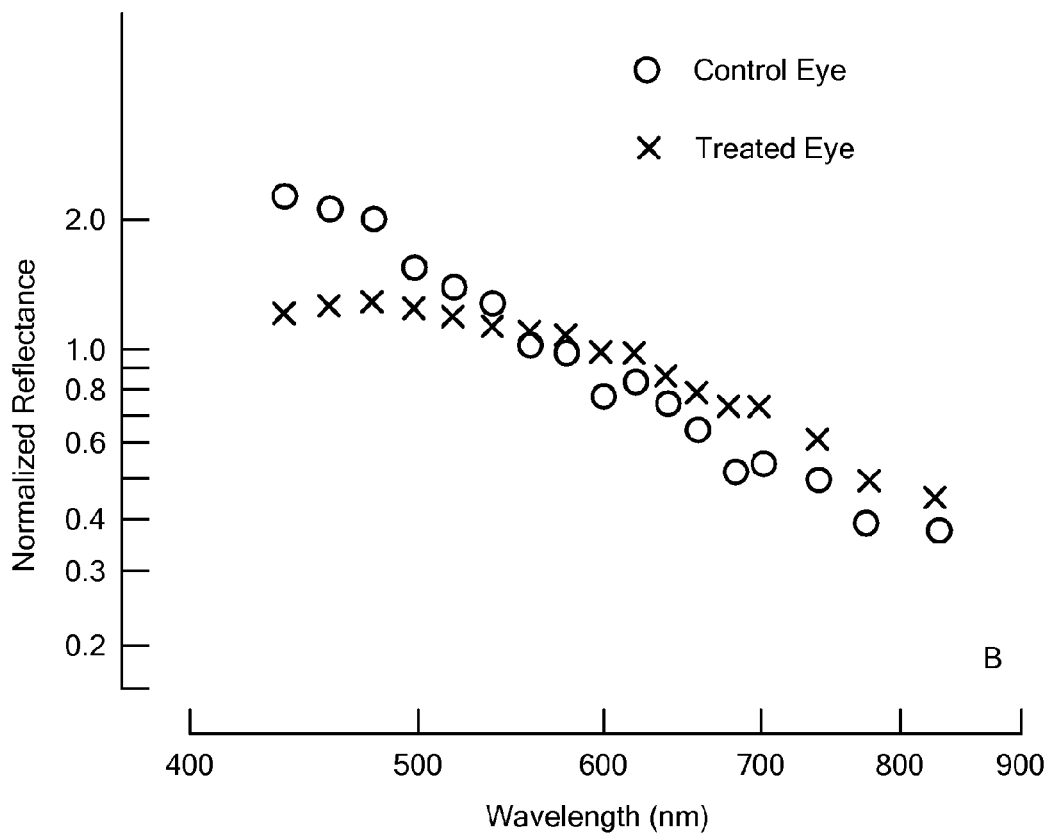
FIG. 1 is a graph illustrating reflectance spectra of a glaucomatous eye and a control eye.

FIG. 1 is a graph illustrating RNFL reflectance spectra of a normal rat eye and a rat eye that was exposed to high IOP for 28 days with peak IOP of 48 mmHg. The data in FIG. 1 shows that damage characteristic of early stage glaucoma changes the RNFL spectrum and is detectable before any significant changes in thickness of the RNFL. RNFL spectra also differ from that of surrounding tissue, allowing wavelength contrast detection of RNFL to augment segmentation and provide more accurate thickness measurements.

FIG. 1 shows a normal RNFL reflectance spectrum, which has a characteristic rise at short wavelengths. At wavelengths less than 560 nm, the reflectance of damaged RNFl decreases significantly compared to longer NIR wavelengths. Reflectance spectra of human RNFL shares these characteristics with the rat eye shown here. Thus, the present invention provides an analytic tool for ophthalmology.

The present invention detects early glaucoma damage preferably using a dual-band OCT scanner, which utilizes both a band of visible light to detect the decrease in short wavelength reflectance and a band of NIR light to provide a reflectance reference and to image retinal structures. Optionally, more than two bands of wavelength of light may be utilized to detect and characterize the reflectance spectra of the RNFL. For example, 1050 nm light is also used in OCT scanning and can be used in addition to or in place of the 830 nm light described herein to provide the present invention. The ratio of the reflectance intensities at 830 nm and 105 nm may also aid in segmenting the retina and detecting damage.

The dual-band OCT scanner of the invention is preferably a high-resolution SD (spectral domain)-OCT device which optionally includes a spectrometer and a fiber interferometer to image the RNFL of an animal or human. One fiber broad spectrum light source may be the light source, or any light source that covers a spectrum from 460 nm to 2500 nm. The output of the light source may then be split into two beams, the first beam being filtered at visible wavelength (for example, 500 nm) while the second beam being filtered at NIR (for example 830 nm). Alternatively, a broad spectrum beam may be applied to the eye being studied and only the reflectance of the diagnostic wavelengths measured.

The beam delivery system may be similar to those used in current commercial OCT systems, making the dual-band OCT system compatible with existing platforms. For example, the dual-band OCT delivery system may be built on a commercial slit-lamp, which may be further used in routine eye examinations. The sample light beams are then collimated from two optical fiber based interferometers and are coupled by a beam combiner. Those skilled in art will appreciate that there are a variety of suitable beam combiners for combining two bands of light for use in OCT scanning. For example, the beam combiner may be a hot mirror, which reflects IR light but transmits visible light.

The combined sample light may then be scanned by means of an X-Y galvanometer optical scanner and delivered to the eye. Alternatively, the beam combiner may be used to combine the original source beams so that a single interferometer may be used.

Figure 2:
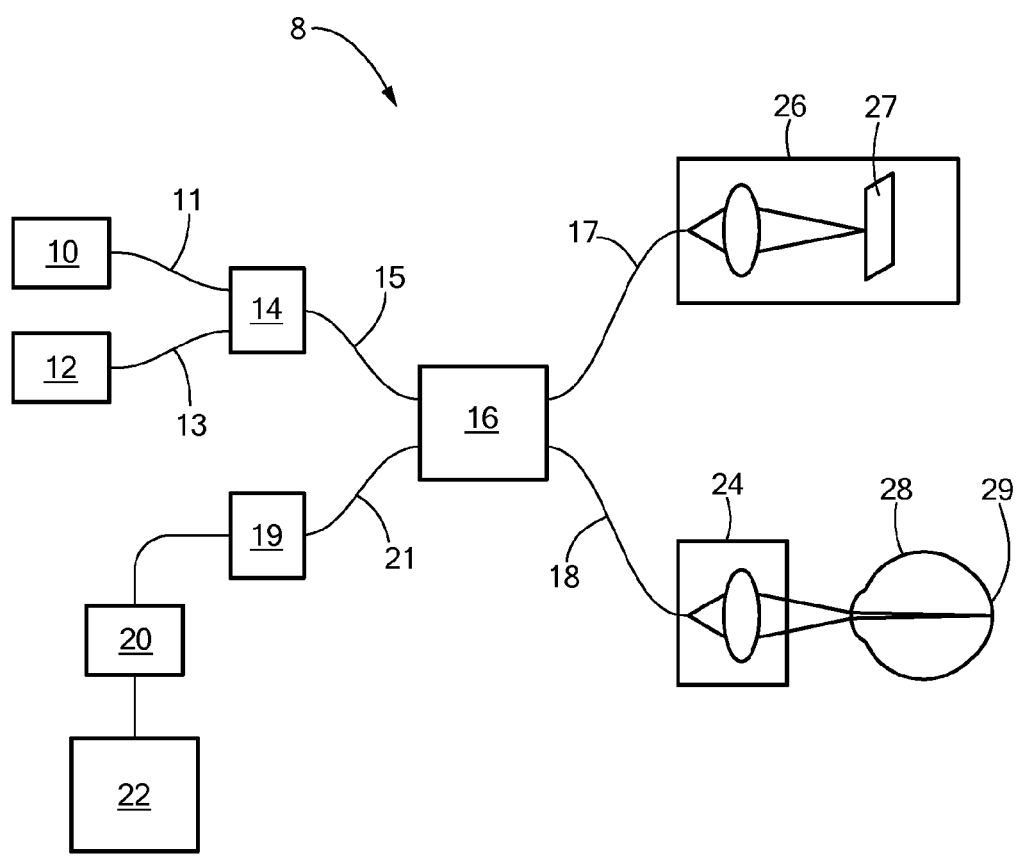
FIG. 2 is a schematic of a dual-band OCT scanner system.

FIG. 2 shows a diagram of a typical OCT scanner system 8 that has been modified by adding a second source of light to provide a second beam of light having a different wavelength range. Other devices for reading light reflected from a retina, such as a fundus camera or SLO device may also be used for the present invention. However, existing OCT systems are easily modified to provide the present invention.

In this example, light source 10 provides a band of light in the near infrared region (NIR). This band is centered around 830 nm wavelength light, just beyond the visible region and may range from about 780 nm to about 880 nm. NIR light in this range is generally preferred for OCT retina scanning as only a portion of the band is visible as a dim red light and does not irritate a patient. However, longer NIR wavelengths, e.g. around 1000-1050 nm, are also used in standard OCT scanning and are also suitable for use as the NIR band of the present invention. Reflectance by the retina is substantially constant across the NIR spectrum and therefore any band of NIR light is suitable for one of the two beams of light. However, in this example the commonly used band around 830 nm is used.

While OCT scanner 8 uses two light sources 10 and 12, one fiber super-continuum or broad band light source may also be used. The output of the light source may then be split into two beams, the first beam being filtered at visible wavelength, e.g. 500 nm, while the second beam being filtered at NIR, e.g. 830 nm.

Light source 12 provides a band of light in the visible region centered around a wavelength of 500 nm Generally such light is avoided in OCT systems as visible light may irritate the eye. In this example, light source 12 produces a band of light ranging from about 480 nm to about 520 nm. Bands in the shorter wavelengths of visible light, for example a band ranging from 400-460 nm, are also suitable for the invention. Because this light is visible, it may be desirable to optionally include a shutter in the invention to block this light beam except when the actual scanning is performed. This reduces irritation to the eye being analyzed.

The embodiment shown in FIG. 2 shows two light sources, one providing a band around 500 nm and one providing a band around 830 nm. It may be desirable to include a third band of light around 1050 nm. Similarly, inclusion of other bands of light may also be desirable to perform more detailed and broader analysis of the retinal spectra.

The beam of 830 nm light from source 10 travels through optic fiber 11 to beam combiner 14. Similarly, the beam of 500 nm light from source 12 travels through optic fiber 13 to beam combiner 14. Beam combiner 14 may include a hot mirror, which reflects IR light but transmits visible light. Beam combiner 14 combines the two beams into a single beam of light, with peaks at 500 and 830 nm. And transmits the single beam through optic fiber 15 to interferometer 16.

Interferometer 16 is a typical fiber interferometer that splits the combined beam into two separate beams. One beam is sent through optic fiber 17 to reference arm 26. Reference arm 26 includes adjustable reference mirror 27 that allows the system to conduct an optical coherence tomography scan. Those skilled in the art will appreciate that other types of interferometers suitable for optical OCT will also be suitable for the present invention.

Interferometer 16 also sends a beam through optic fiber 18 to sample arm 24. Sample arm 24 includes an X-Y scanner for scanning an eye 28. The X-Y scanner allows the sample arm 24 to direct the beam of light to individual pixels about the retina 29 in the eye 28. A pixel as used herein is defined as an area on the surface of the retina 29 and extends through the entire depth of the retina 29. Thus the X-Y scanner moves the OCT beam across a plurality of pixels, each of which is scanned at a plurality of depths in order to create a three dimensional dataset. Those skilled in the art will appreciate that there are several types of OCT scanners, some of which use full-field systems that accumulate light from a plurality of pixels at once and do not require an X-Y scanner. Full-field systems scan several pixels simultaneously all at the same depth. The reference mirror is then adjusted and the pixels are all scanned again at the new depth. This process is repeated and is faster than OCT systems using an X-Y scanner. The recorded intensities of the reflected light from each of the pixels at a given depth create a cross sectional tomogram. By combining these tomograms a three dimensional image of the retina is formed.

Light reflected from the eye 28 returns to the sample arm 24 and travels back to interferometer 16. There, it is combined with light reflected off adjustable reference mirror 27 and returning from reference arm 26. Those skilled in the art will appreciate that the light beams from the reference and sample arms constructively and destructively interfere with each other to produce a beam of light having an intensity dependent on the amount of light reflected from the sample at a particular depth corresponding to the position of the reference mirror 27. The strength of interfering light transmitted to the detector 19 is indicative of the reflectance of the target object at a depth into the object corresponding to the position of adjustable reference mirror 27.

The combined beam travels through optic fiber 21 to photodetector 19 which converts the intensity of the beam into an electrical signal. As the X-Y scanner and adjustable mirror are actuated, the intensity of the reflected light is converted by photodetector 19 to record intensity levels for a plurality of pixels on the retina 29 at a plurality of depths. A data processor 20 then uses this data to create several tomograms for each depth level of the retina and may also combine these tomograms to form a three dimensional image of the retina. If a full-field OCT system is utilized, the photodetector 19 will comprise an array of detectors placed in a sensing plane. This allows an entire level-slice to be recorded simultaneously.

The RNFL reflectance, R, may then be calculated for each of the two bands of light for various regions or layers of the retina. The wavelength ratio may then also be calculated from the acquired three-dimensional OCT dataset. The wavelength ratio, also called the normalized reflectance, is calculated by dividing the reflectance of the light in the visible, 500 nm band by the reflectance of the light in the NIR, 830 nm band for a particular region of the retina.

The intensity of an OCT image at a particular pixel at a particular depth can be expressed as $I_{OCT}(x, y, z, \lambda)$, where x, y, and z are the horizontal, vertical, and depth coordinates, $\lambda$ is the center wavelength of the light source, the RNFL reflectance, R, at different wavelengths can be expressed as $$R(x, y, \lambda_1) = \sum_{z(ILM)}^{z(GCL)} I_{OCT}(x, y, z, \lambda_1)$$

and $$R(x, y, \lambda_2) = \sum_{z(ILM)}^{z(GCL)} I_{OCT}(x, y, z, \lambda_2),$$

where $R(x, y, \lambda_1)$ and $R(x, y, \lambda_2)$ are the RNFL reflectance at center wavelengths of 500 nm and 830 nm, respectively, z(ILM) and z(GCL) are the depth coordinates of the inner limiting membrane (ILM) and the ganglion cell layer (GCL) respectively. $R(x, y, \lambda_1)$ is generally referred to as $R_1$ and $R(x, y, \lambda_2)$ is generally referred to as $R_2$. The measured value of R may also be calculated for a single pixel as a summation or it may be calculated as the average over several pixels in two or three dimensions. Comparing the relative RNFL reflectance quantitatively among different measurements may be difficult, unless the reflectance is normalized against a reference. An advantage of the dual-band OCT system of the present invention is that the reflectance at 830 nm may be used as a reference to normalize the reflectance at $$500 \text{ nm}: \frac{R_1(x, y, \lambda_1)}{R_2(x, y, \lambda_2)}.$$

The normalized reflectance image at different time points may then be compared to detect damage to the RNFL. The wavelength ratio calculated by normalizing the reflectance of the 500 nm band may be used to identify regions of damage to the RNFL. A low wavelength ratio, at or near 1:1 indicates damaged RNFL, while higher ratio values around 2:1 indicate a healthy RNFL. The wavelength ratio is therefore used to detect early damage as $R_1$ decreases relative to $R_2$.

As part of the OCT imaging method, the RNFL reflectance of band may be normalized with the reflectance of the other band, to eliminate uncontrolled factors, such as focusing, media opacities, and surface reflections that can affect the reflectance measurement. This allows clear three dimensional imaging of the RNFL or other regions of the retina. Furthermore imaging of the summed and normalized reflectances above provides a two dimensional image of RNFL damage.

Because the eye is sensitive to visible light, the OCT in the NIR band may be used for alignment and optimizing imaging parameters. During the aligning process the visible band may be blocked with a shutter. After the alignment process, when the image acquisition mode is activated, the visible band may be briefly initiated and images in both bands will be acquired. This improves both patient comfort and safety during an eye examination.

The depth resolution of the dual-band OCT system enables focusing on the reflection from RNFL only while accounting for the reflection from other layers of the retina. Because of the complexity and number of retinal structures, segmenting the retinal layers may be necessary to accurately measure the reflectance from the RNFL.

A first segmenting method may include imaging the portion of the retina between the ILM and the lower boundary between the RNFL and the ganglion cell layer (GCL). The RNFL reflection may then be calculated by summation of the pixel intensity inside the segmented layer.

A second segmentation method may include imaging the portion between the ILM and the INL. The INL appears dark in an OCT image, and the RNFL is the major reflection layer between the ILM and INL. This method may have an advantage in areas containing thick RNFL with poor signal strength, for example, due to directional reflectance. The spectrum of this segmented layer, which contains mostly RNFL, may then be evaluated for the presence of abnormal spectrum. As such, measuring the reflection between the ILM to the INL is essentially measuring the reflectance from the RNFL. Additionally, the INL may be easily segmented for imaging, and the need for segmentation accuracy during image acquisition may be relatively low because the INL is dark in an OCT image.

The OCT system of the present invention may be similar in design to those used in current commercial OCT systems, making the dual-band OCT system compatible with existing platforms. For example, the dual-band OCT system may be built on a commercial slit-lamp, which may be further used in routine eye examinations.

While an OCT scanner was utilized in the example of FIG. 1, other spectral detection methods capable of measuring the reflected light from two or more wavelength bands may be utilized to detect changes or damage to the RNFL and to discriminate RNFL from other tissue. For example, the dual-band imaging method may also be applied in fundus camera imaging, a scanning laser ophthalmoscope (SLO), or hyperspectral fundus imaging. As applied to these technologies, dual wavelengths may be used to enhance the RNFL contrast by suppressing spectral components of deeper layers (for example, the choroid) containing melanin and blood. In a fundus camera, for example, different filters may be used to acquire fundus images at different bands. The images may then be normalized by dividing the intensity image in one hand by the images in another hand. For a SLO, different laser sources can be used in a single system to acquire the fundus reflection at different bands. These methods do not distinguish depth and as such may only be used for constructing two dimensional images. Nonetheless, they are still effective at identifying early damage to the RNFL as indicated by a drop in reflectance of visible light.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of analyzing a retina comprising:
    applying visible and near-infrared light to the retina;
    measuring an intensity of light reflected at a plurality of depths for each of a plurality of pixels of the retina within a first band of visible light;
    measuring an intensity of light reflected at a plurality of depths for each of the plurality of pixels of the retina within a second band of near-infrared light;
    comparing the intensity of light reflected within the first band and the intensity of light reflected within the second band:
    defining a retinal nerve fiber layer;
    segmenting the retina based on the defined retinal nerve fiber layer;
    summing the intensities of the reflected light of the first band at each depth within the retinal nerve fiber layer for each of the plurality of pixels to calculate a reflectance, $R_1$, of the first beam for the retinal nerve fiber layer;

summing the intensities of the reflected light of the second band at each depth within the retinal nerve fiber layer for each of the plurality of pixels to calculate a reflectance, $R_2$ of the second beam for the retinal nerve fiber layer; and dividing $R_1$ by $R_2$ to calculate a wavelength ratio for each of the pixels of the retina.

2. The method of claim 1, wherein the first band comprises wavelengths between approximately 480 and 520 nanometers and the second band comprises wavelengths between approximately 780 and 880 nanometers.

3. The method of claim 1 further comprising:
providing a fundus camera;
applying light to the retina from the fundus camera; and
forming a two dimensional image of the retina based on the measured intensity of light reflected within the first band and the second band.

4. The method of claim 1, further comprising:
providing a scanning laser ophthalmoscope;
applying light to the retina from the laser opthalmoscope; and
measuring the intensity of light reflected within the first band and the second band.

5. The method of claim 1, wherein the first band of light comprises light having wavelengths between approximately 480 and 580 nanometers, the second band of light comprises light having wavelengths between approximately 780 and 880 nanometers, and applying light to the retina and measuring the intensity of light reflected within the first band and the second band are performed using one of the devices selected from the group consisting of a fundus camera, a scanning laser ophthalmoscope and an optical coherence tomography device.

6. A method of analyzing a retina comprising:
performing an optical coherence tomography scan of the retina with a first beam of visible light;
measuring the intensity of light of the first beam reflected at a plurality of depths for each of a plurality of pixels within the retina;
performing an optical coherence tomography scan of the retina with a second beam of near-infrared light;
measuring the intensity of the light of the second beam reflected at a plurality of depths for each of the plurality of pixels within the retina for the second beam;
comparing the intensities of the reflected light of the first beam and the reflected light of the second beam;
defining a retinal nerve fiber layer;
segmenting the retina based on the defined retinal nerve fiber layer;
summing the intensities of the reflected light of the first beam at each depth within the retinal nerve fiber layer for each of the plurality of pixels to calculate a reflectance, $R_1$, of the first beam for the retinal nerve fiber layer;
summing the intensities of the reflected light of the second beam at each depth within the retinal nerve fiber layer for each of the plurality of pixels to calculate a reflectance, $R_2$, of the second beam for the retinal nerve fiber layer; and dividing $R_1$ by $R_2$ to calculate a wavelength ratio for each of the pixels of the retina.

7. The method of claim 6, wherein the light of the first beam comprises a band of light having wavelengths between approximately 480 and 520 nanometers and the second beam comprises a band of near-infrared light having wavelengths between approximately 780 and 880 nanometers.

8. The method of claim 6, wherein the optical coherence tomography scan with the first beam and the optical coherence tomography scan with the second beam are performed substantially simultaneously.

9. The method of claim 6, further comprising creating a three dimensional image of the retina.

10. The method of claim 6 wherein defining the retinal nerve fiber layer includes designating a region of the retina where the intensity of the reflected light of the first band is substantially greater than the reflected light of the second band.

11. The method of claim 6, further comprising creating an image of the retinal nerve fiber layer using the calculated wavelength ratios.

12. The method of claim 11, wherein the light of the first beam comprises a band of light having wavelengths between approximately 480 and 520 nanometers and the second beam comprises a band of near-infrared light having wavelengths between approximately 780 and 880 nanometers and the optical coherence tomography scan with the first beam and the optical coherence tomography scan with the second beam are performed substantially simultaneously.

13. The method of claim 8, wherein the performing optical coherence scanning with the first and second beams is performed by a device comprising:
at least one light source producing at least a first scanning beam and a second scanning beam;
an interferometer that divides the first and second scanning bands into first and second reference beams emitted toward a reference arm and first and second sample beams emitted toward a retina, and receives and combines first and second reflected reference beams and first and second reflected sample beams to produce first and second interference beams having optical intensities;
an X-Y scanner directing the first and second sample beams to a plurality of pixels on the retina;
an adjustable reference mirror within the reference arm allowing measurement of reflected light from a plurality of depths for each of the plurality of pixels;
a detector measuring the intensities of the first and the second interference beams and converting them into first and second intensity signals; and
a signal processor accumulating the first and second intensity signals for each of the plurality of pixels at each of the depths to create a three dimensional dataset.

* * * * *